US008911962B2

(12) United States Patent
Lovern

(10) Patent No.: US 8,911,962 B2
(45) Date of Patent: Dec. 16, 2014

(54) METHOD FOR NEUTRALIZATION OF ANTIBIOTICS IN A CULTURE MEDIUM

(71) Applicant: Douglas Lovern, Durham, NC (US)

(72) Inventor: Douglas Lovern, Durham, NC (US)

(73) Assignee: bioMerieux, Inc., Durham, NC (US)

(*) Notice: Subject to any disclaimer, the term of this patent is extended or adjusted under 35 U.S.C. 154(b) by 0 days.

(21) Appl. No.: 14/069,576

(22) Filed: Nov. 1, 2013

(65) Prior Publication Data

US 2014/0234889 A1    Aug. 21, 2014

Related U.S. Application Data

(62) Division of application No. 13/772,965, filed on Feb. 21, 2013, now Pat. No. 8,603,770, which is a division of application No. 12/827,241, filed on Jun. 30, 2010, now Pat. No. 8,420,346.

(60) Provisional application No. 61/269,953, filed on Jul. 1, 2009.

(51) Int. Cl.
C12Q 1/04    (2006.01)
C12Q 1/02    (2006.01)

(52) U.S. Cl.
CPC .................................. *C12Q 1/025* (2013.01)
USPC ............................................. 435/34; 435/29

(58) Field of Classification Search
USPC ..................................................... 435/34, 29
See application file for complete search history.

(56) References Cited

U.S. PATENT DOCUMENTS

| | | | |
|---|---|---|---|
| 3,497,504 A | | 2/1970 | Wagner |
| 4,145,304 A | | 3/1979 | Melnick et al. |
| 4,174,277 A | | 11/1979 | Melnick et al. |
| 4,212,948 A | | 7/1980 | Dorn |
| 4,221,871 A | | 9/1980 | Meitzner et al. |
| 4,632,902 A | | 12/1986 | Waters et al. |
| 5,094,955 A | | 3/1992 | Calandra et al. |
| 5,108,927 A | | 4/1992 | Dorn |
| 5,162,229 A | * | 11/1992 | Thorpe et al. .............. 435/288.7 |
| 5,164,796 A | | 11/1992 | Di Guiseppi et al. |
| 5,217,876 A | | 6/1993 | Turner et al. |
| 5,314,229 A | | 5/1994 | Matuzawa et al. |
| 5,518,895 A | | 5/1996 | Thorpe et al. |
| 5,624,814 A | | 4/1997 | Waters et al. |
| 5,795,773 A | | 8/1998 | Read et al. |
| 5,856,175 A | | 1/1999 | Thorpe et al. |
| 5,858,769 A | | 1/1999 | DiGuiseppi et al. |
| 2003/0170264 A1 | | 9/2003 | Turner et al. |
| 2008/0286310 A1 | | 11/2008 | Zhu et al. |
| 2009/0123960 A1 | * | 5/2009 | Rosenstein et al. ............ 435/29 |

FOREIGN PATENT DOCUMENTS

WO    2008133659    11/2008

OTHER PUBLICATIONS

Kahan, J.S. et al. Thienamycin, a new beta-lactam antibiotic, Journal of Antibiotics XXXII (1978).
Beadle, Beth M. et al. Structural basis for imipenem inhibition of class C beta-lactamases, Antimicrobial Agents and Chemotherapy 46:3978-3980 (2002).
Beadle, Beth M. et al. Interaction energies between beta-lactam antibiotics and *E. coli* penicillin-binding protein 5 by reversible thermal denaturation, Protein Science 10:1254-1259 (2001).
Monks, Joan et al. Imipenem as substrate and inhibitor of beta-lactamases, Biochem. J. 253:323-328 (1988).
Mainardi, Jean-Luc et al. Unexpected Inhibition of Peptidoglycan LD-Transpeptidase from *Enterococcus faecium* by the beta-Lactam Imipenem, J. Biol. Chem. 282(42):30414-30422 (2007).
The International Search Report for PCT/US2010/040522 dtd Mar. 28, 2011.
The International Search Report and Written Opinion for PCT/US2010/040552 dtd Mar. 28, 2012.
Sierra-Madero, et al. "Detection of Bacteria in the Presence of Antibiotics by Using Specific Monoclonal Antibodies to Neutralize the Antibiotics", Journal of Clinical Microbiology, pp. 1904-1906. vol. 26, No. 9. (1988).
Nakken, et al. "The Mechanism of Inactivation of Penicillin by Cysteine and Other Mercaptoamines", Biochemical Pharmacology. pp. 89-100, vol. 3 (1960).
Murray, et al. "Inactivation of Penicillins by Thiol Broth", Journal of Clinical Microbiology, pp. 982-984. vol. 16, No. 5 (1982).
Stevens, et al. "Simple Method for Elimination of Aminoglycosides from Serum to Permit Bioassay of Other Antimicrobial Agents", pp. 286-287, vol. 12, No. 2 (1977).

* cited by examiner

*Primary Examiner* — Karen Cochrane Carlson
*Assistant Examiner* — Natalie Moss

(57) ABSTRACT

The present invention is directed to a method and means for the neutralization, binding, and/or inactivation of antimicrobials in a test sample. The invention is also directed to a method of detecting the presence of one or more microorganisms in a test sample by culturing the test sample in a culture media comprising one or more primary amine-containing compounds.

7 Claims, 5 Drawing Sheets

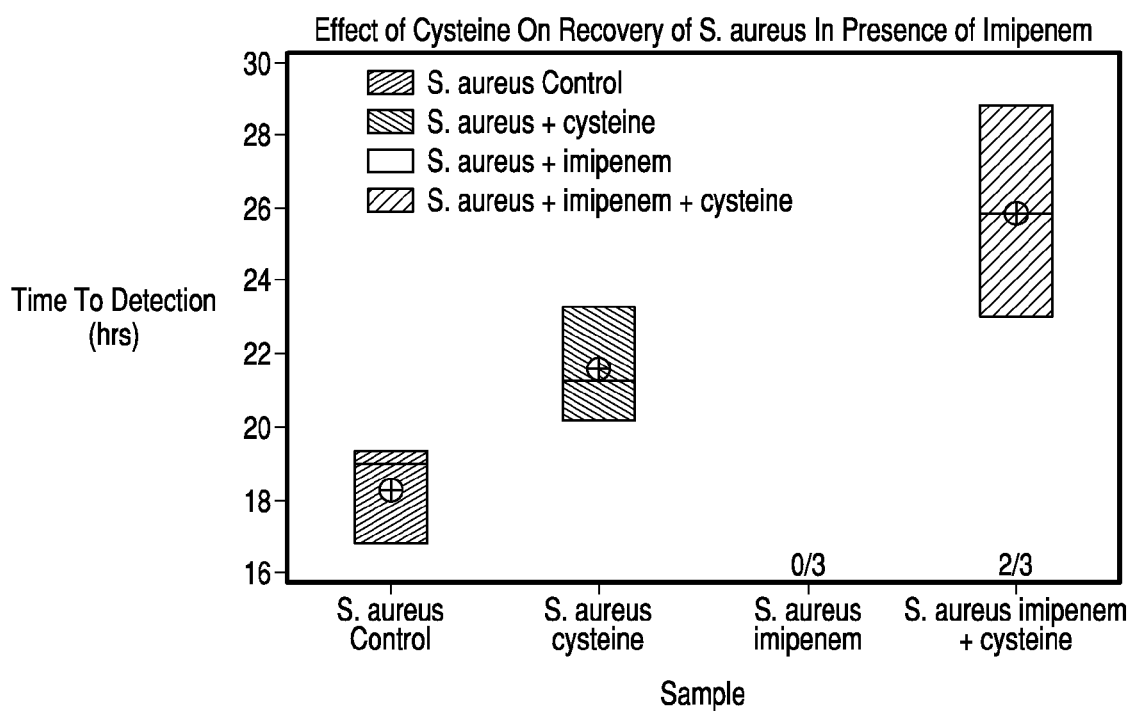

METHOD FOR NEUTRALIZATION OF ANTIBIOTICS IN A CULTURE MEDIUM

CROSS REFERENCE TO RELATED APPLICATION

This application is a divisional application of currently pending U.S. patent application Ser. No. 13/772,965, which is a divisional application of U.S. patent application Ser. No. 12/827,241, which issued as U.S. Pat. No. 8,420,346 Apr. 16, 2013, and claims the benefit of U.S. provisional patent application No. 61/269,953, entitled, "Method for Neutralization of Antibiotics in a Culture Medium", filed Jul. 1, 2009, which is incorporated herein.

FIELD OF THE INVENTION

The present invention is directed to the neutralization and/or inactivation of antibiotics in a test sample or culture medium. The present invention is also directed to a method of culturing and detecting microorganisms that may be present in a test sample.

BACKGROUND OF THE INVENTION

In the field of culturing and detecting microorganisms, specialized culture bottles and machines for holding the culture bottles are typically used for detecting the presence of microorganisms in a test specimen. Bottles, such as those disclosed in U.S. Pat. Nos. 4,945,060; 5,094,955; and 5,162,229, herein incorporated by reference, have a culture medium and a sensor in the interior of the bottle that undergoes a detectable change due to the growth of microorganisms present in the bottle. The change in the sensor is monitored from outside the culture bottle through the transparent wall of the culture bottle, such as with a light emitter and detector as disclosed in, for example, U.S. Pat. Nos. 5,164,796 and 5,217,876, herein incorporated by reference. For most assays, the culture bottles should be agitated for best results. Clips, such as those disclosed in U.S. Pat. No. 5,074,505, herein incorporated by reference, can hold the culture bottles in place in the incubating machine during agitation.

The detection of pathogenic microorganisms in biological fluids should be performed in the shortest possible time, in particular in the case of septicemia for which the mortality remains high in spite of the broad range of antibiotics which are available to doctors. In order to increase sick individuals' chances of survival, practitioners often administer an antibiotic or mixture of antibiotics to the patients. It is, however, important to determine a suitable antibiotic therapy as soon as possible. Unfortunately, when a patient's bodily fluid sample is cultured to identify and isolate an infecting microorganism that might be present, antibiotics previously administered to the patient can interfere with the culturing process. Furthermore, medical samples may contain serum, plasma and lysed erythrocytes that may naturally contain microbial inhibitors. Industrial samples such as pharmaceuticals and foods may also contain antimicrobials or preservatives that inhibit the growth of microorganisms. Additionally, when culture media is prepared, autoclaving of the media at very high temperatures under pressure can result in the formation of by-products toxic to microorganisms. Removal or neutralization of these inhibitory or bactericidal substances is necessary to detect microbial contamination.

The use of resins and non-resinous adsorbents is well known and has been previously described for use in medical diagnostic procedures. In particular, these resins and non-resinous adsorbents have been shown useful in the removal of antibiotics and other antimicrobials from blood samples. The removal of these inhibitors in medical samples allows for recovery and faster detection of microorganisms so that microbial identification and accurate antibiotic susceptibility testing can be performed.

Melnick et al., U.S. Pat. No. 4,145,304, herein incorporated by reference, describes the use of synthetic anionic exchange and nonionic resins to remove antimicrobials, including antibiotics, from body fluids, thus allowing for recovery of pathogens using standard culture techniques. The resins described are coated with a nonionic detergent in order to selectively remove charged antibiotics while inhibiting adherence of bacteria to the resins. After treatment of the sample with the resin, the eluate is cultured in a growth media. The degree of binding of antibiotics by the resins is indicated to be dependent on the total exchange capacity, pore diameter, and surface area of the resin.

Waters, U.S. Pat. No. 4,632,902, herein incorporated by reference, describes an improvement over Melnick by incorporating ion exchange resins and non-functional adsorbent resins directly into the growth medium. Inhibitors removed include antibiotics administered to patients and naturally occurring inhibitors contained in serum, plasma, and lysed erythrocytes. The resins are not coated with a nonionic detergent or surfactant before use and the pore size of the resin is not critical.

Thorpe et al., U.S. Pat. Nos. 5,162,229 and 5,314,229, herein incorporated by reference, describe the use of resin and non-resinous adsorbents to neutralize, bind, or inhibit antimicrobial substances that may be present in a biological sample. The resin and non-resinous adsorbents described include, aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene and combinations thereof.

Although synthetic resins and non-resinous adsorbents are known to remove inhibitory substances in cultures containing body fluids, these resins and non-resinous adsorbents may be ineffective in neutralizing or removing some types of antibiotics. For example, some $\beta$-lactams are commonly used in the treatment of sepsis and their presence in blood samples can interfere with the recovery, detection and identification of the microorganism responsible for the sepsis. In particular, resins and non-resinous adsorbents currently used in the art to remove antimicrobials from blood samples have proven largely ineffective in neutralizing carbapenems. It is therefore desirable to find other means for the neutralization or inhibition of antibiotics in body fluids and non-body fluid samples, such as foods and industrial products.

The present invention provides a means for the neutralization or inhibition of antimicrobials in test samples, while helping to retain the components of the medium necessary to recover and detect microorganisms in a rapid manner. By finding a means for the neutralization and/or inactivation of $\beta$-lactams (e.g., carbapenems) that previously could not be effectively neutralized or inactivated in a culture medium, the present invention solves a long-felt need in the art.

SUMMARY OF THE INVENTION

In one aspect, the present invention involves a means or method involving the use of one or more primary amine-containing compounds to neutralize, bind, inhibit or otherwise inactivate an antimicrobial substance (e.g., one or more antibiotics) in a growth or culture medium. In one embodiment, the present invention is directed to the neutralization, inhibition or inactivation of one or more antibiotics with one or more primary amine-containing compounds in culture medium (e.g., a blood culture).

The present invention is also directed to a method for the neutralization and/or inactivation of an antimicrobial in a culture medium (e.g., a blood culture) comprising adding one or more primary amine-containing compounds to a culture medium which is capable of supporting growth of microorganisms, wherein said one or more primary amine-containing compounds are present in an amount effective neutralizes and/or inactivates any carbapenems present in said culture medium. In one embodiment, the antimicrobial is a carbapenem. In another embodiment, the primary amine is a non-thiol containing primary amine.

In another aspect, the present invention is directed to a method for enhanced recovery and detection of microorganisms in culture, the method comprising: (a) preparing culture medium; (b) adding to the medium at least one primary amine-containing compound in amounts that are effective for neutralizing, binding or inhibiting antimicrobial substances in the culture medium; (c) inoculating the medium with a sample; and (d) incubating and determining the results. In one embodiment, the antimicrobial is a carbapenem. In another embodiment, the primary amine is a non-thiol containing primary amine.

In still another aspect, the present invention is directed to a method for the diagnosis of an infection caused by a microorganism, comprising the steps of: (a) obtaining a specimen sample or test sample for which the presence or absence of a microorganism is to be determined, and wherein said specimen or test sample may contain one or more antimicrobials that may interfere with the growth and/or detection of the microorganism; (b) adding said specimen sample or test sample to a culture medium, said culture medium comprising at least one primary amine-containing compound in an amount that is effective for neutralizing, binding or inhibiting said one or more antimicrobials; and (c) analyzing said culture for the presence of said microorganism, wherein detection of the presence of said microorganism indicates a positive diagnosis for said infection. In one embodiment, the antimicrobial is a carbapenem. In another embodiment, the primary amine is a non-thiol containing primary amine. In still another embodiment, detection of said microorganism comprises detection of the growth of said microorganism in said culture medium.

In yet another aspect, the present invention is directed to a device for detecting microorganisms suspected of being in a specimen comprising a sealable specimen container comprising an internal chamber in which the specimen may be cultured in a culture medium, said culture medium containing at least one primary amine-containing compound, wherein said primary amine-containing compound neutralizes and/or inactivates antibiotics that may be present in said specimen.

In still another aspect, the present invention is directed to a kit for detecting microorganisms in a test sample, the kit comprising: (1) a sealable specimen container, having an internal chamber comprising a culture medium and in which a test sample, for which the presence or absence of a microorganism is to be determined, may be cultured; and (2) a supplement comprising one or more primary amine-containing compounds. In accordance with this aspect of the present invention, the supplement can be added to the culture medium contained in the sealable specimen container, thereby providing the one or more primary amine-containing compounds in an amount that is effective for neutralizing, binding or inhibiting any antimicrobials that may be present in said culture medium. A test sample can be added to the culture medium, concurrently with, or after addition of the supplement to the culture medium, the supplement providing the one or more primary amine-containing compounds in an amount that is effective for neutralizing, binding or inhibiting any antimicrobials that may be present in said test sample.

BRIEF DESCRIPTION OF THE FIGURES

FIG. 3—is a boxplot showing the effect of cysteine on the recovery of *S. aureus* in the presence of imipenem.

DETAILED DESCRIPTION OF THE INVENTION

Figure 1A:
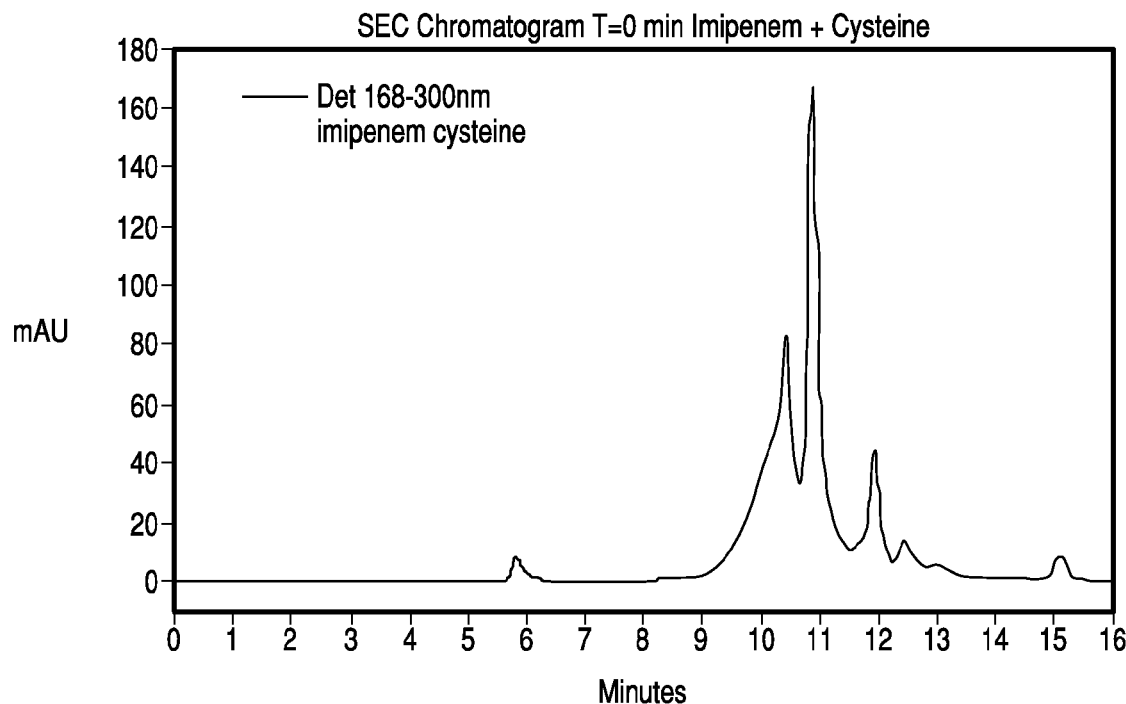
FIG. 1A—is a Size Exclusion Chromatography (SEC) Chromatogram of imipenem in the presence of cysteine after a reaction time of 0 min.

The present invention provides methods for detecting the presence of microorganisms in a specimen or test sample containing or suspected of containing microorganisms. In accordance with this invention, the methods involve a chemical neutralization method involving the use of primary amine-containing compounds to neutralize, bind, inhibit or otherwise inactivate an antimicrobial substance (e.g., antibiotics) in a growth or culture medium. In one embodiment, the present invention is directed to the neutralization, inhibition or inactivation of one or more antibiotics with a primary amine-containing compound in blood culture medium. In some embodiments, the primary amine-containing compound may be a non-thiol containing compound and/or a hydroxylamine.

Samples that may be tested by the methods of the invention include both clinical and non-clinical samples in which microorganism presence and/or growth is or may be suspected, as well as samples of materials that are routinely or occasionally tested for the presence of microorganisms. Test samples can typically range from about 0.5 ml to about 50 ml, from about 1 ml to about 10 ml, or from about 2 ml to about 5 ml.

Clinical specimens or specimen samples that may be tested include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. In one embodiment of the present invention, samples are obtained from a subject (e.g., a patient) having or suspected of having a microbial infection. In one embodiment, the subject has or is suspected of having septicemia, e.g., bacteremia or fungemia. The sample may be a blood sample taken directly from the subject.

Non-clinical samples that may be tested also include substances, encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial, commercial, and/or clinical settings.

A first aspect of the invention relates to methods for the neutralization and/or inactivation of antibiotics using one or more primary amine-containing compounds. The method comprises adding one or more primary amine-containing compounds to a growth or culture medium in an effective amount to neutralize, bind, and/or inhibit one or more antibiotics present, or suspected of being present, in a test sample. The one or more primary amine-containing compounds can be added to the growth or culture media prior to, or concurrently with, innoculation of the growth or culture media with a test sample. Although, not wishing to be bound by theory, it is believed that the use of a primary amine-containing compound provides a chemical means for neutralization of antimicrobials, whereby the primary amine interacts or binds with the β-lactam ring structure of the antibiotic. The primary amine may carry out a nucleophilic attack on the β-lactam ring forming a covalent complex leading to the inactivation and/or neutralization of the β-lactam antibiotic. After inoculation, the growth or culture media and test sample can be incubated for a sufficient time and at a sufficient temperature to allow for the growth and detection of any microorganism that may be present in the test sample. Growth can be detected by any known means in the art. For example, growth can be detected using a BacT/ALERT® or BacT/ALERT® 3D systems (bioMerieux, Inc.). The time and temperature required for growth of the microorganism are largely species specific, but typically will be from about 1 hour to about 48 hours and from about 30° C. to about 42° C.

An "effective amount" means the use of a sufficient amount of a compound to neutralize, bind, and/or inhibit the activity of one or more antibiotics present, or suspected of being present, in a test sample or culture media. An "effective amount" can be an amount sufficient to produce a measurable inhibition of one or more antibiotics present in a test sample or medium. Inhibition of antibiotics can be measured in vitro by high-performance liquid chromatography (HPLC), or by other methods known to one skilled in the art. An "effective amount" can also be an amount sufficient to show detectable microorganism growth in a test sample or culture media containing an antibiotic whose activity would otherwise suppress or eliminate detectable growth. An "effective amount" may not need to be an amount that would totally eliminate the activity of one or more antibiotics present, or suspected of being present in the growth or culture media. Rather, in the practice of the present invention, the use of an "effective amount" of one or more primary amine-containing compounds in a growth or culture media allows for the growth or cultivation of microorganisms that would otherwise be surpressed or eliminated from the presence of one or more antibiotics that are neutralized, bound, and/or inhibited by the primary amine-containing compound, in accordance with the present invention. Typically, an "effective amount" of one or more primary amine-containing compounds is an amount allowing for a final concentration in the growth of culture media of from about 0.1 g/L to about 20 g/L, from about 0.5 g/L to about 10 g/L, or from about 1 g/L to about 5 g/L.

In one embodiment, the present invention is a method for enhanced recovery and detection of microorganisms in culture, the method comprising: (a) preparing culture medium; (b) adding to the medium at least one primary amine-containing compound in amounts that are effective for neutralizing, binding or inhibiting antimicrobial substances in the culture medium; (c) inoculating the medium with a sample to be tested; and (d) incubating and determining the results. In another embodiment, the present invention is also directed to a method for the neutralization and/or inactivation of a carbapenem in a blood culture comprising adding a primary amine-containing compound to a blood culture medium which is capable of supporting growth of microorganisms, wherein said primary amine-containing compound neutralizes and/or inactivates any carbapenems present in said culture medium.

In another aspect, the present invention relates to a method for the diagnosis of an infection caused by a microorganism, comprising the steps of: (a) obtaining a test sample for which the presence or absence of a microorganism is to be determined, and wherein said test sample may contain one or more antimicrobials which may interfere with the growth and/or detection of the microorganism; (b) adding said test sample to a culture medium, said culture medium comprising at least one primary amine-containing compound in an amount that is effective for neutralizing, binding or inhibiting said one or more antibiotics; and (c) analyzing said culture for the presence of said microorganism (e.g., detection of said microorganism or the growth of said microorganism), wherein a finding of the presence of said microorganism indicates a positive diagnosis for said infection. After adding the test sample to the growth or culture media, the growth or culture media and test sample can be incubated for a sufficient time and at a sufficient temperature, as is well known to those skilled in the art, to allow for the growth and detection of any microorganism that may be present in the test sample. Growth can be detected by any known means in the art. For example, growth can be detected using a BacT/ALERT® or BacT/ALERT® 3D systems (bioMerieux, Inc.). Growth readings can be taken continuously or a give time intervals.

In general, any known antibiotic can be neutralized using the methods of the present invention. In one aspect, the present invention is directed to the use of a primary amine-containing compounds to neutralize and/or inactivate a β-lactam antibiotic. β-lactam antibiotics are a broad class of antibiotics that include any antibiotic agent that contains a β-lactam nucleus in its molecular structure. β-lactam antibiotics include, but are not limited to, penicillins, penicillin derivatives, cephalosporins, monobactams, carbapenems, and β-lactamase inhibitors.

In one embodiment, primary amine-containing compounds can be used to neutralize and/or inactivate penicillin and penicillin derivative antibiotics. Penicillins are a class of β-lactam antibiotics known as penams. Penams are a group of antibiotics sharing a similar core skeleton ($R-C_9H_{11}N_2O_4S$, where R is a variable side chain). Penicillins and penicillin derivatives include, for example, benzathine penicillin, benzylpenicillin (penicillin G), phenoxymethylpenicillin (penicillin V), procaine penicillin, oxacillin, methicillin, nafcillin, cloxacillin, dicloxacillin, flucloxacillin, temocillin, amoxycillin, ampicillin, azlocillin, carbenixillin, mezlocillin, and piperacillin.

In another embodiment, primary amine-containing compounds can be used to neutralize and/or inactivate cephalosporins and cephalosporin derivatives. Cephalosporins are a group of β-lactam antibiotics sharing a core skeleton comprising 7-aminocephalosporanic acid. Cephalosporins and cephalosporin derivatives include, for example, cephalexin, cephalothin, cefazolin, cefaclor, cefuroxime, cefamandole, cefotetan, cefoxitin, ceftrizxone, cefotaxime, cefpodoxime, ceftazidime, cefepime, and cefpirome.

In yet another embodiment, primary amine-containing compounds can be used to neutralize and/or inactivate carbapenem and carbapenem derivatives. Carbapenems are a class of β-lactam antibiotics with a broad spectrum of antibacterial activity, and have a structure that renders them resistant to β-lactamases. Carbapenems and carbapenem derivatives include imipenem, meropenem, ertapenem, doripenem, panipenem, betamipron, biapenem, and PZ-601. The carbapenems are somewhat structurally similar to the penicillins, but the sulfur atom in position 1 of the structure has been replaced with a carbon atom, and hence the name of the group, the carbapenems. Nevertheless, this seemingly subtle structural difference can lead to dramatic different effects in chemical and biological activity.

In still another embodiment, primary amine-containing compounds can be used to neutralize and/or inactivate β-lactamase inhibitors and derivatives of β-lactamase inhibitors. β-lactamase inhibitors and derivatives include, for example, calvulanic acid, tazobactam and sulbactam.

As previously mentioned, in accordance with this invention, the primary amine-containing compound can be added to a growth or culture media. The primary amine-containing compound can be added directly to the media prior to, or concurrently, with inoculation of the medium with a sample to be tested. In another embodiment, the primary amine-containing compound can be added directly to the sample to be tested, prior to the sample being added to the growth or culture medium.

The use of a growth or culture media (or medium) for the cultivation of microorganisms is well known. A suitable growth or culture medium provides the proper nutritional and environmental conditions for growth of microorganisms and should contain all the nutrients required by the microorganisms which are to be cultivated. For example, a typical microbiological culture medium should contain water, a carbon source, a nitrogen source, vitamins, trace elements such as potassium, magnesium, calcium and iron, and minerals, such as sulfur and phosphorous. Typically, these needs are supplied from a number of sources. Other factors for suitable propagating conditions may include pH, temperature, aeration, salt concentration and osmotic pressure of the medium.

In addition, it is known that certain growth factors may be required. A growth factor is an organic compound which a microorganism must contain in order to grow but which it is typically unable to synthesize. Many microorganisms, when provided with the nutrients listed above, are able to synthesize all of the organic constituents of their protoplasm, including amino acids, vitamins, purines and pyrimadines, fatty acids and other compounds. Typically, each of these essential compounds can be synthesized by a discrete sequence of enzymatic reactions, where each enzyme is produced under the control of a specific gene. However, for a variety of reasons some microorganism cannot synthesis one or more of these growth factors and must then obtain that compound from the environment. Required growth factors may include, but are not limited to, amino acids, vitamins, purines and pyrimadines, fatty acids and other required compounds for growth.

The growth or culture media used in the practice of the present invention can be any known growth of culture media for the cultivation of microorganisms. Typically, the culture medium of the present invention comprises a liquid nutrient medium or nutrient broth. The culture medium or nutrient broth of the present invention typically comprises one or more known nutrients, for example, the culture medium may contain one or more carbon sources (e.g., glycerol), nitrogen sources (e.g., ammonia salts), sugars, salts (e.g., $K^+$, $Mg^{2+}$, $Ca^{2+}$, $Zn^{2+}$), nutrients, and/or water. In one embodiment, the culture medium of the present invention may further comprise one or more of potassium salts, sodium salts, sodium glutamate, sodium citrate, ammonium sulfate, pyridoxine, ferric ammonium citrate, magnesium sulfate, zinc sulfate, copper sulfate, biotin, calcium chloride, or combinations thereof. In another embodiment, general purpose medias can be used, include, for example, tryptic soy broth, brain heart infusion broth, Columbia broth, and Brucella broth.

In general, any known primary amine-containing compound can be used in the practice of the present invention. As discussed hereinabove, one or more primary amine-containing compounds can be added to the growth or culture media prior to, or concurrently with, inoculation of the growth or culture media with a test sample. In one embodiment, the primary amine-containing compound can be added as a supplement to the culture medium prior to the inoculation of the primary amine-containing culture medium with a sample to be tested. In an alternative embodiment, the primary amine-containing compound can be added directly to the test sample prior to inoculation of the culture medium with the primary amine-containing test sample. Useful primary amines include, but are not limited to, a primary amine of the formula R—$NH_2$ where R is a linear or branched alkyl, aryl, alkaryl, or aralkyl group having between about 1 and about 20 carbon atoms. Preferred R groups include, without limitation, methyl, ethyl, propyl, isopropyl, butyl, sec-butyl, isobutyl, hexyls (linear or branched), hepyls, octyls, nonyls, decyls, phenyl, benzyl, methyl substituted phenyls, or mixtures or combinations thereof. In one embodiment, the primary amine is a hydroxylamine Exemplary primary amines may include methylamine, ethanolamine, trisamine, propylamine, 2-aminoheptane, 2-amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, α-methylbenzylamine, phenethylamine, isopropylamine, butylamine, sec-butylamine, iso-butylamine, and tris(hydroxymethyl)aminomethane.

In some embodiments, organic primary amines may be preferred. Suitable organic primary amines may include aliphatic, cycloaliphatic, aliphatic/aromatic, aromatic amines, diamines and/or polyamines, such as methylamine, ethylamine, butylamine, stearylamine, aniline, halogen-substituted phenylamines (e.g., 4-chlorophenylamine), 1,4-diaminobutane, 1,6-diaminohexane, 1,8-diamino-hexane, 1-amino-3,3,5-trimethyl-5-aminocyclohexane, lysine ethyl ester, lysine aminoethyl ester, 1,6,11-triaminoundecane or 1,5-naphthylenediamine, 1,4-diaminobenzene, p-xylylenediamine, perhydrogenated 2,4- and/or 2,6-diaminotoluene, 2,2'-, 2,4'- and/or 4,4'-diaminodicyclohexylmethane, 2,4-, 2,6-diaminotoluene and their mixtures, 4,4'-, 2,4'- and/or 2,2'-diphenylmethanediamine and their mixtures, as well as higher molecular weight isomeric, oligomeric or polymeric derivatives of these amines and polyamines Other possible amines are known from the prior art. Preferred amines for the present invention are the diamines and polyamines of the diphenylmethane series (MDA, monomeric, oligomeric and polymeric amines), 2,4-, 2,6-diaminotoluene (TDA, toluoylenediamines), for example technical mixtures of 2,4-, 2,6-diaminotoluene (TDA, toluoylenediamines) in a weight ratio of 80:20, isophorone diamine and hexamethylenediamine. The corresponding isocyanates diisocyanatodiphenylmethane (MDI, monomeric, oligomeric and polymeric isocyanates), toluene diisocyanate (TDI), hexamethylene diisocyanate (HDI) and isophorone diisocyanate (IPDI) are obtained in the phosgenation.

In other embodiments, the primary amine can be an amino acid. Exemplary amino acids include, but are not limited to, alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine.

In some embodiment, the use of a hydroxylamine may be preferred. As one of skill in the art is well aware, hydroxylamines generally include compounds having the formula $NH_2OH$, and salts thereof. Exemplified useful hydroxylamines include, but are not limited to, methanolamine, ethanolamine, propanolamine, butanolamine, pentanolamine, hexanolamine, heptanolamine, octanolamine, nonanolamine and decanolamine.

Thiol groups or sulfhydryl groups tend to be scavengers of oxygen, and thus, may interfere with components of a growth or culture media and/or microorganism growth in a growth or culture media. As such, in some embodiments the use of one or more non-thiol containing primary amines may be preferred. As one of skill in the art is well aware, non-thiol containing primary amines may include any known primary amine-containing compounds that does not contain a thiol group. Exemplary non-thiol containing primary amines include, but are not limited to, methylamine, ethanolamine, trisamine, propylamine, 2-aminoheptane, 2-amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, α-methylbenzylamine, phenethylamine, isopropylamine, butylamine, sec-butylamine, iso-butylamine, and tris(hydroxymethyl) aminomethane. In yet other embodiment, the use of a non-thiol containing amino acid may be preferred. Useful non-thiol containing amino acids include, but are not limited to, alanine, arginine, asparagine, aspartate, glutamate, glutamine, glycine, histidine, isoleucine, leucine, lysine, phenylalanine, proline, serine, threonine, tryptophan, tyrosine, and valine.

In another embodiment, the primary amine can be bound to, or immobilized on, a solid support or a polymeric carrier, and the primary amine-support complex added to a culture medium or bottle, as discussed herein. In general, the support may be any material on which a binding partner can be immobilized, such as nitrocellulose, silica, polystyrene, polypropylene, polyvinyl chloride, EVA, glass, carbon, glassy carbon, carbon black, carbon nanotubes or fibrils, platinum, palladium, gold, silver, silver chloride, iridium, or rhodium. In one embodiment, the solid support can be, polymeric carriers, for example modified silica gel, glass, especially "controlled pore glass", polyester, polyamide, polyvinyl alcohol, polysiloxane, polystyrene or the like. In another embodiment, useful solid supports may include, but are not limited to, silica and neutral macroporous resins such co-polymers of styrene and divinylbenzene.

In another aspect of the present invention, the growth or culture media may further comprise one or more adsorbents for the neutralization, inhibition and/or removal of additional antimicrobial substances that may be present in a test sample. Generally, antimicrobial substances include, among others, antibiotics, antibiotics in body fluid samples, preservatives, bacteriostats, bactericides, and any toxic by-products produced during the preparation of culture media. Antimicrobial substances also include naturally occurring components in blood such as complement and antibodies.

The term "adsorbent" for the purposes of this application, includes all adsorbent materials that neutralize, bind, and inhibit antimicrobial substances. These adsorbents include resins and non-resinous adsorbents as defined in U.S. Pat. Nos. 4,145,304; 4,632,902; 5,162,229; and 5,314,229.

As used herein, "resin" is a subclass of adsorbents, and is further defined to include naturally occurring and synthetic resins, for example ion exchange resins, non-functional polymeric resin adsorbents and, in particular, polystyrene resins cross-linked with divinyl benzene. Useful resins can include, but are not limited to, those disclosed in U.S. Pat. Nos. 4,145,304 and 4,632,902. For example, useful resins may include sodium, hydrogen and ammonium charged cation exchange resins such as: BIO REX AG 50W—$X_2, X_4, X_6, X_8, X_{10}, X_{12}$, and $X_{16}$ from BIO-RAD Laboratories, DOWEX 50W—$X_2$, $X_4, X_6, X_8, X_{10}, X_{12}$, and $X_{16}$ from Dow Chemical Company and Rexyn 101 from Fisher Scientific Co., all of which are strong acid polystyrene resins having $SO^{3-}$ functional group. Useful non-functional resins may include XAD resins manufactured by Rohm & Haas and SM resins sold by BioRad. For example, chloride, formate, acetate and hydroxide, charged anion exchange resins have generally been found to be suitable. Specifically, chloride charged anionic exchange resins in combination with adsorbent resins sold under the following trademarks may be effective in the practice of the invention. DOWEX 1-X8 from Dow Chemical Company, DUOLITE A-109 from Diamond Shamrock Company and AMBERLITE IRA400 from Rohm & Haas, all of which are strong base resins having polystyrene quaternary ammonium functional groups; DUOLITE A-7 from Diamond Shamrock Company and AMBERLITE IR45 from Rohm & Haas, which are weakly basic and have tertiary amine functional groups. In some embodiments, the cation and anion exchange resins may preferably be used in combination with a non-functional resin such as the XAD resins from Rohm & Haas and SM resin from BioRad, particularly XAD-4 resin which is a nonfunctional copolymer of styrene and divinyl benzene.

As used herein "non-resinous adsorbents" are another subclass of adsorbents and are defined as naturally occurring and synthetic non-resin adsorbents and molecular sieves that can be used for clarifying, deodorizing, decolorizing, and filtering. Some of these non-resinous adsorbents are the same as those used during the production of antibiotics to remove antibiotics from culture medium growing antibiotic-producing bacteria. Useful non-resinous adsorbents include those disclosed in U.S. Pat. Nos. 5,162,229 and 5,314,229. For example, useful non-resinous adsorbents include various forms of 1) aluminum oxide (alumina), 2) colloidal native hydrated aluminum silicates (clays), such as bentonite, kaolin, and fuller's earth, 3) crystalline hydrated alkali-aluminum silicates (sodium or calcium zeolites), 4) silica (silica gel, silica beads) such as Davisil, 5) siliceous frustules and fragments of various species of diatoms (infusorial earth, diatomaceous earth) such as Celite™ (Manville Products Corporation, Denver, Colo., USA) and 6) amorphous carbon (in particular, activated carbon) such as Carboraffin, Norit™ (American Norit Company Inc., Jacksonville, Fla., USA), Opocerbyl, and Ultracarbon. Naturally occurring adsorbent activated charcoal, which has been used to prevent the lethal effects of oxidation in transport media and growth media, can also be used. This media has been used for the transport of fastidious organisms such as *Neisseria gonorrhoeae* and the cultivation of *Legionella* species. Non-resinous adsorbents do not require pre-treatment with a surfactant in order to function. Treatment with surfactants may even decrease the adsorptive capabilities of these materials.

The use of adsorbents at an appropriate ratio to medium may also remove toxic by-products produced in autoclaved media and still provide an optimal nutritious culture medium while maintaining the ability to neutralize antimicrobial substances. The resins and/or non-resinous adsorbents may be present in the culture media from about 0.1 g to about 10 g per bottle.

The present adsorbents are not limited to use in a device or culture bottle. They may be added to any standard culture media, which is then inoculated with a sample, incubated at the correct temperature for an appropriate time for the type of sample being tested, while usually shaken or rocked in order to expose more surface area of the adsorbent to the liquid, to better contact any organisms present with nutrients and to avoid areas of high concentration of metabolic by-products. The temperatures and time periods needed for the determination of microorganism growth are well known to those skilled in the art and vary somewhat among different types of organisms.

In another aspect, the present invention is directed to a device for detecting microorganisms suspected of being in a test sample or specimen comprising a sealable container comprising an internal chamber in which the test sample or specimen may be cultured in a growth or culture medium, said growth or culture medium containing at least one primary amine-containing compound, wherein said primary amine-containing compound neutralizes, binds and/or inactivates one or more antibiotics (e.g., carbapenems) present in said specimen. In one embodiment, the device is a blood culture bottle, as described, for example, in U.S. Pat. Nos. 5,094,955 and 5,162,229. In accordance with this aspect of the present invention, a test sample is introduced into the device, and the device is incubated until either positive growth is detected or, generally, until 5-7 days have passed and no growth is detected.

In another embodiment, the primary amine-containing compound can be included in a supplement that can be added to the culture medium prior to, or concurrently with inoculation of the culture medium with the sample to be tested. In an alternative embodiment, the primary amine-containing supplement can be added directly to the test sample, prior to inoculation of the bottle and culture media with the primary amine-containing test sample. The supplement may further comprise one or more nutrients and/or components known to those of skill in the art as being beneficial to the cultivation of microorganisms. For example, the supplement of the present invention may additionally comprise of one or more sugars, carbon sources, nitrogen sources, minerals, salts, amino acids, vitamins, purines and pyrimadines, fatty acids and other compounds. After addition of the supplement and inoculation of the culture medium with the sample to be tested, the culture media and sample can be cultivated for a sufficient time and at a sufficient temperature to allow for the growth and detection of any microorganism that may be present in the test sample.

In still another aspect, the present invention is directed to a kit for detecting microorganisms in a test sample, the kit comprising: (1) a sealable specimen container, having an internal chamber comprising a culture medium and in which a test sample, for which the presence or absence of a microorganism is to be determined, may be cultured; and (2) a supplement comprising one or more primary amine-containing compounds. In accordance with this aspect of the present invention, the supplement can be added to the culture medium contained in the sealable specimen container, thereby providing the one or more primary amine-containing compounds in an amount that is effective for neutralizing, binding or inhibiting any antimicrobials that may be present in said culture medium. A test sample can be added to the culture medium, concurrently with, or after addition of the supplement to the culture medium, the supplement providing the one or more primary amine-containing compounds in an amount that is effective for neutralizing, binding or inhibiting any antimicrobials that may be present in said test sample. The supplement of the kit further comprises a second container or vial comprising the one or more primary amine-containing compounds. In one embodiment, the second container or vial comprises the one or more primary amine-containing compounds suspended in a stabilization buffer. Stabilization buffers are well known to those skilled in the art. In another embodiment, the one or more primary amine-containing compounds present in said container or vial can be lyophilized. In accordance with this embodiment, the lyophilized one or more primary amine-containing compounds may be re-suspended in a re-suspension buffer or stabilization buffer prior to being added to the culture medium in the specimen container. In yet another embodiment, the kit of the present invention may further provide a third container or vial comprising said re-suspension or stabilization buffer.

As those of skill in the art are aware, the presence of microorganisms can be determined by detecting or measuring changes in the pH of the specimen or the production of $CO_2$ within a specimen using a disposable sensor affixed to the interior surface of the container, as described, for example, in U.S. Pat. Nos. 4,945,060 and 5,164,796, which are incorporated herein by reference. According to the '060 and '796 disclosures, microorganisms can be detected in the presence of interfering materials, such as large concentrations of red blood cells, through non-radiometric and non-invasive means. As the level of pH and/or $CO_2$ within the specimen changes, the light reflecting and/or absorbing characteristics of the disposable sensor will alter correspondingly. The quantity of alteration of the reflective properties of the sensor is detected by an emission and receiving mechanism which supplies signals to a device for monitoring the quantity of visible reflection/absorption and the rate of change. The rate and quantity is then analyzed to predict and determine the presence of microbial growth within the specimen or sample. The sensor can be sampled and/or monitored continuously or at frequent time intervals allowing for the collection of a detailed characteristic of the quantity and rate of sensor change. As described in the art, the sensor means may comprise a membrane and an indicator medium, the indicator medium being selected for its ability to exhibit a detectable change when exposed to products of an organism's metabolic activity. As known by those skilled in the art, the changes in the appearance of the sensor means can be continuously monitored from the exterior of the container through a transparent section of the container.

This device or blood culture bottle may also include materials in the culture medium such as the resinous materials, as described in U.S. Pat. Nos. 4,145,304 and 4,632,902, and non-resinous adsorbent materials, as described in U.S. Pat. Nos. 5,162,229 and 5,314,229, or combinations thereof, that neutralize, bind, or inhibit any other antimicrobial substances that may be present in the test sample of culture media. The resins and/or non-resinous adsorbents may be present in the device from about 0.1 g to about 10 g per bottle.

The present invention can be embodied in many different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The following examples are given to further illustrate features of the invention, but are not intended to limit the scope of the invention in any way.

EXAMPLES

Example 1

Use of Cysteine to Neutralize Imipenem

A stock solution of USP grade imipenem was prepared by dissolving 1.8 grams in 10 mL of 14 mM $K_2HPO_4$ (pH 7.0) in a glass screw cap tube. A stock solution of cysteine was prepared by dissolving 31.3 mg in 1.08 mL of 14 mM $K_2HPO_4$ in a 2 mL polypropylene centrifuge tube.

An imipenem reaction without cysteine was prepared by combining 2.2 mL of the stock imipenem solution with 7.8 mL of 14 mM $K_2HPO_4$ to a final concentration of 40 μg/mL. The total 10 mL volume was then added to a BacT/Alert culture bottle containing resin adsorbents. The bottle was briefly agitated to mix and 500 μL of volume was removed for analysis. The bottle was then placed in a BacT/Alert® 3D instrument (bioMerieux, Inc., Missouri, USA) at 36° C. and additional 500 μL samples were removed at 20, 40, 60 and 90-minute intervals for analysis (see FIGS. 2A-2D).

Figure 1B:
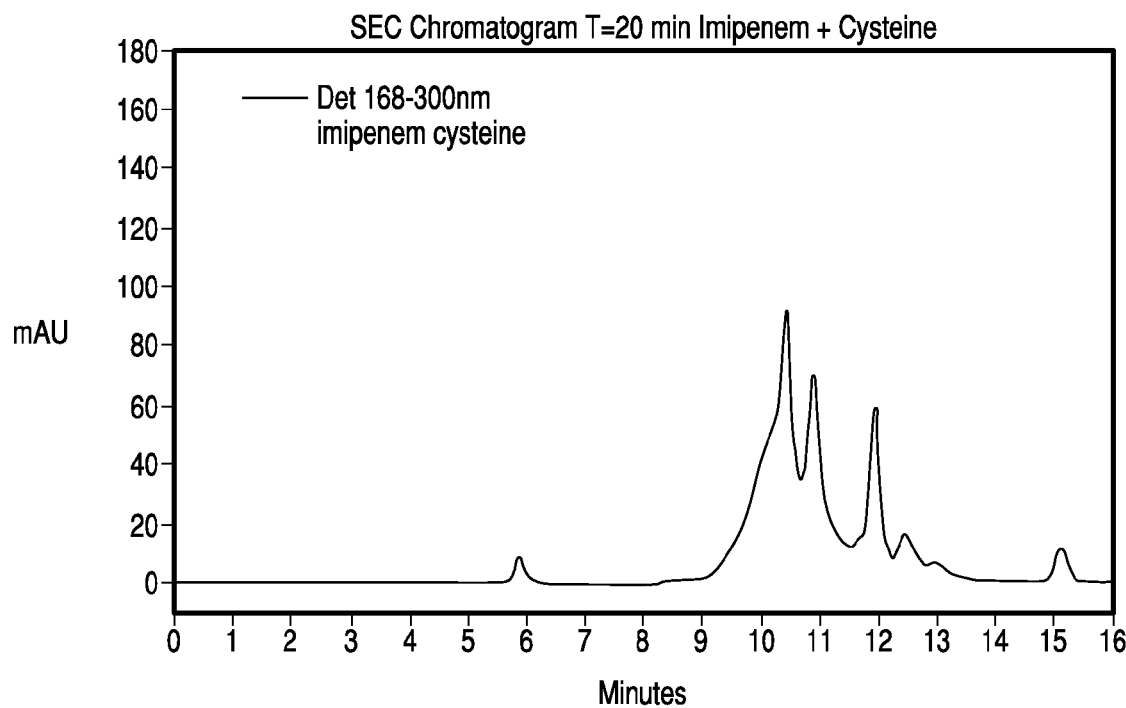
FIG. 1B—is a Size Exclusion Chromatography (SEC) Chromatogram of imipenem in the presence of cysteine after a reaction time of 20 min.
Figure 1C:
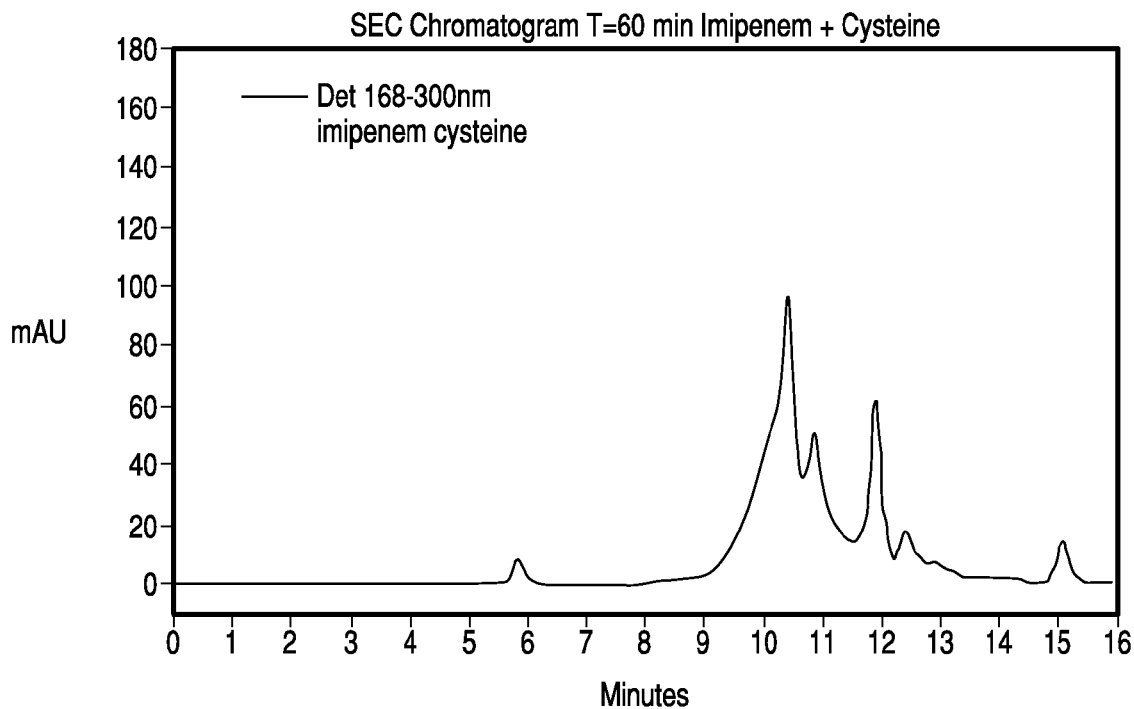
FIG. 1C—is a Size Exclusion Chromatography (SEC) Chromatogram of imipenem in the presence of cysteine after a reaction time of 60 min.
Figure 1D:
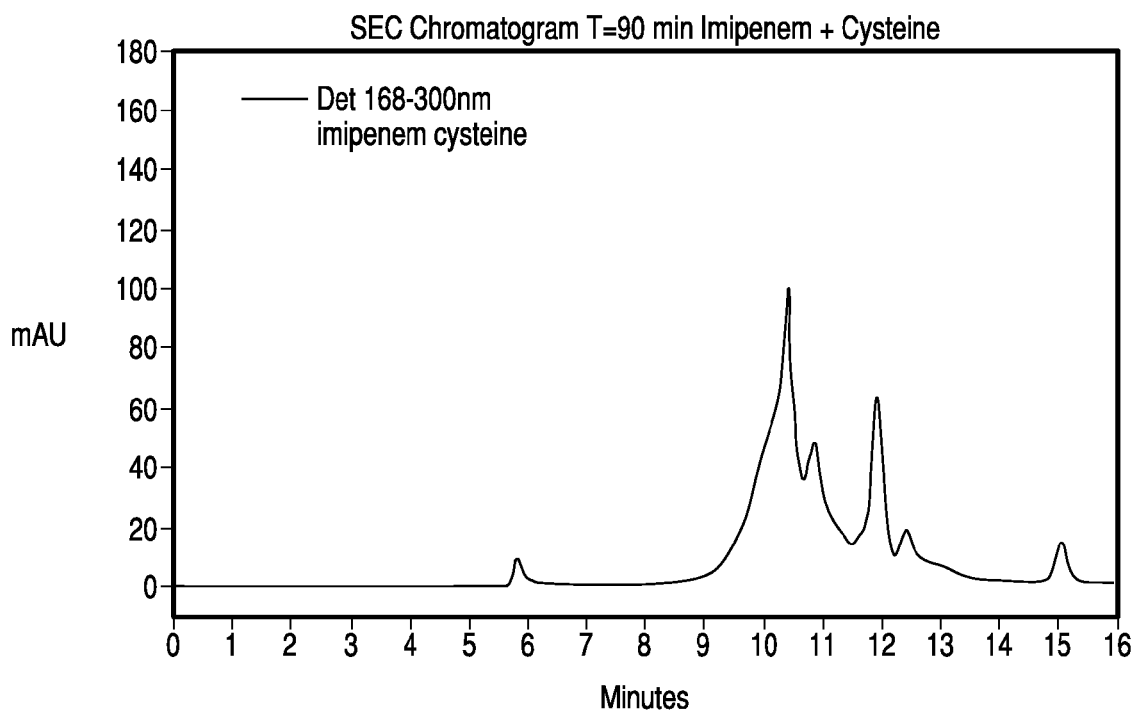
FIG. 1D—is a Size Exclusion Chromatography (SEC) Chromatogram of imipenem in the presence of cysteine after a reaction time of 90 min.
Figure 2A:
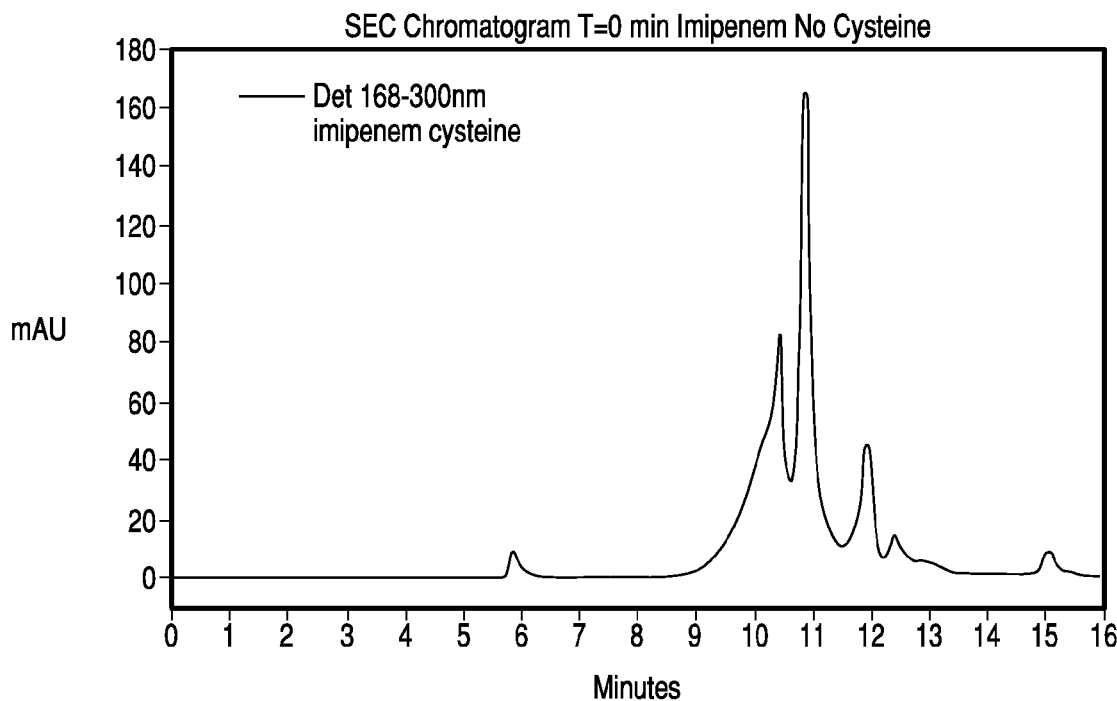
FIG. 2A—is a Size Exclusion Chromatography (SEC) Chromatogram of imipenem, without cysteine after a reaction time of 0 min.
Figure 2B:
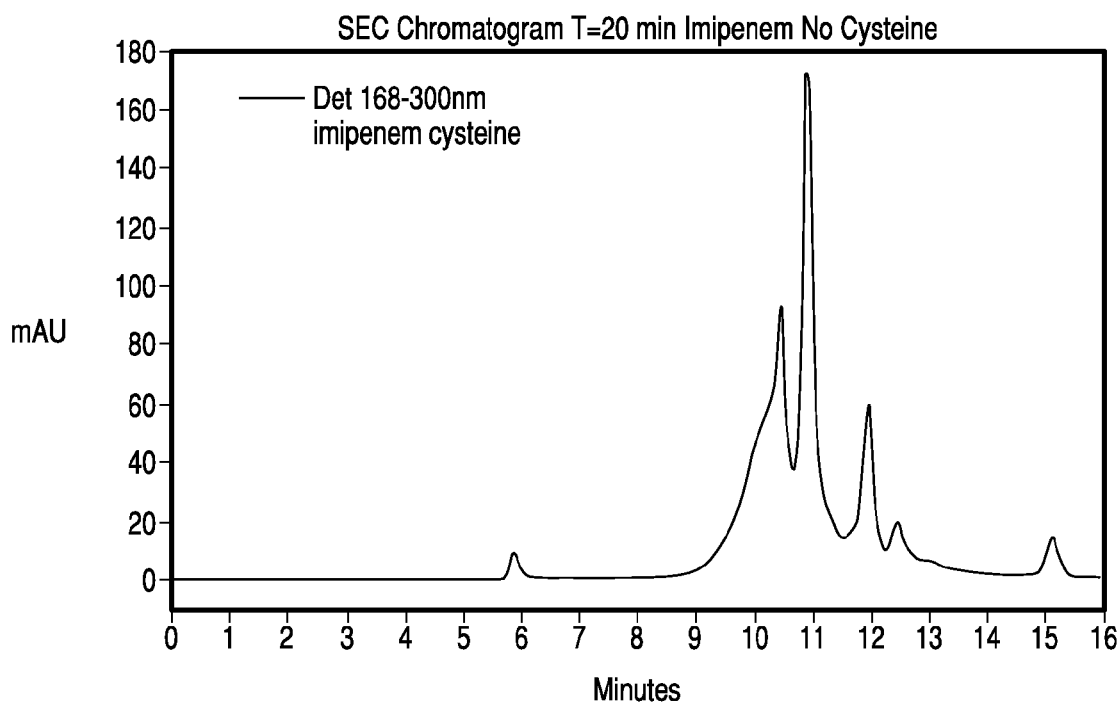
FIG. 2B—is a Size Exclusion Chromatography (SEC) Chromatogram of imipenem, without cysteine after a reaction time of 20 min.
Figure 2C:
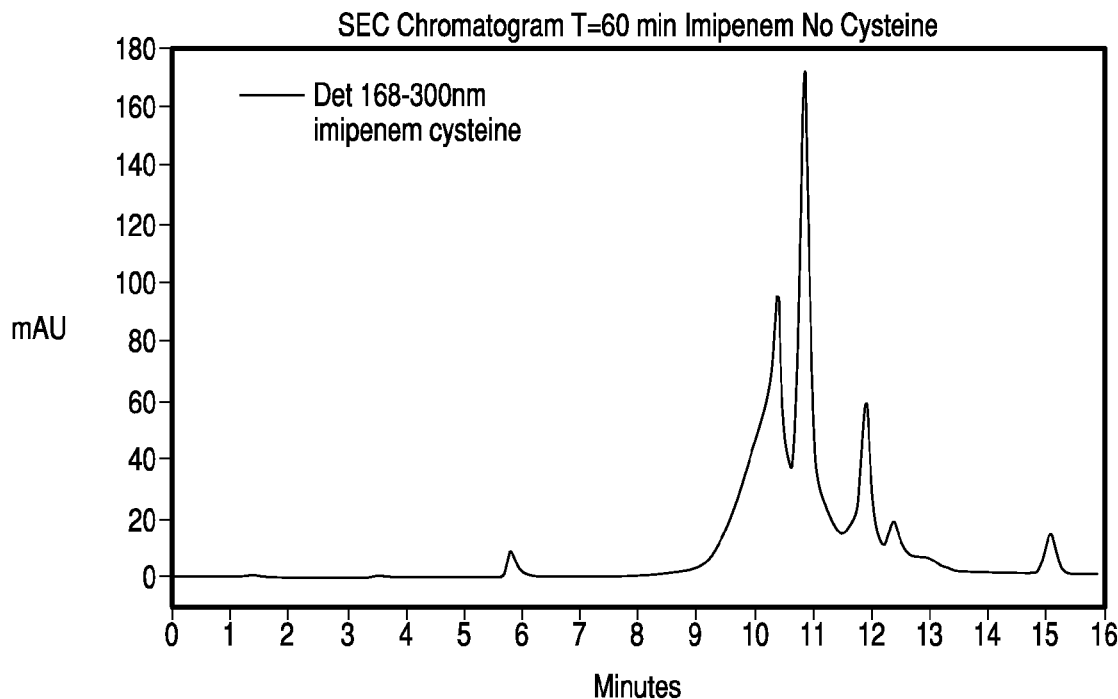
FIG. 2C—is a Size Exclusion Chromatography (SEC) Chromatogram of imipenem, without cysteine after a reaction time of 60 min.
Figure 2D:
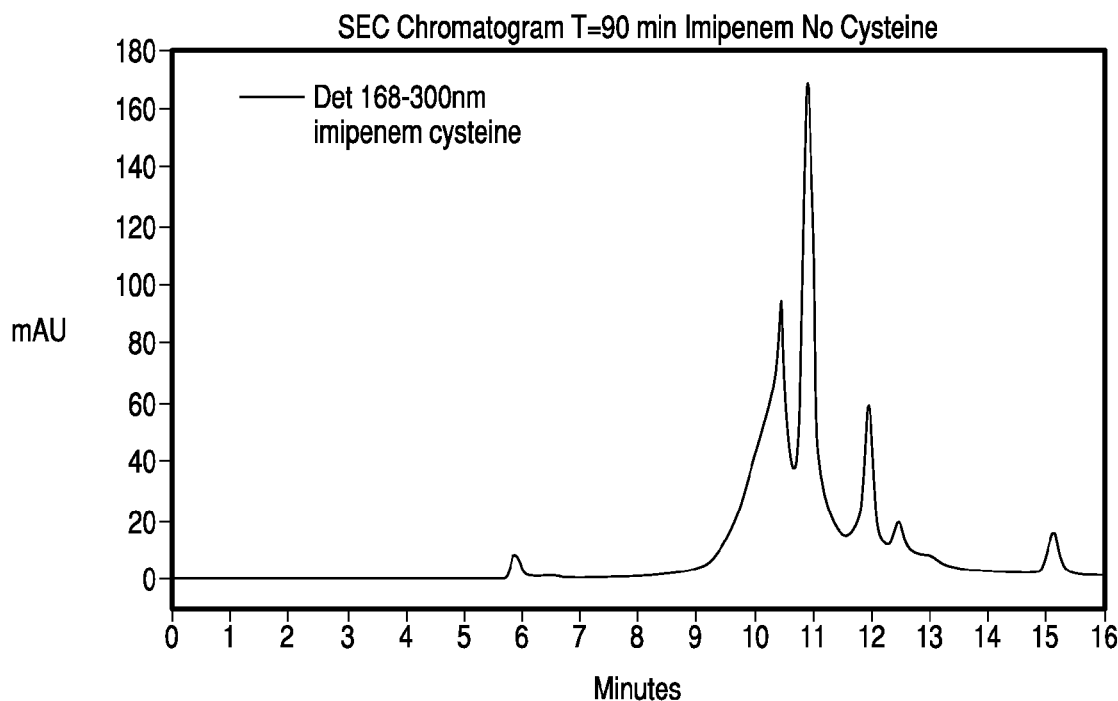
FIG. 2D—is a Size Exclusion Chromatography (SEC) Chromatogram of imipenem, without cysteine after a reaction time of 90 min.

An imipenem reaction with cysteine was prepared by combining 2.2 mL of the stock imipenem solution with 7.8 mL of 14 mM $K_2HPO_4$ to a final concentration of 40 μg/mL. The total 10 mL volume was then added to a BacT/Alert culture bottle containing resin adsorbents. A 500-uL sample of the cysteine stock solution was then added to a final cysteine concentration of 4 mM. The bottle was briefly agitated to mix and 500 μL of volume was removed for analysis. The bottle was then placed in a BacT/Alert® 3D instrument (bioMerieux, Inc., Missouri, USA) at 36° C. and additional 500 μL samples were removed at 20, 40, 60 and 90-minute intervals for analysis (see FIGS. 1A-1B).

Reaction samples were analyzed on an HPLC equipped with a BioSep™-SEC-2000 (Phenomenex) size exclusion HPLC column with a mobile phase of 100 mM $Na_2HPO_4$, ph 6.5 at a 1-mL/minute flow rate. Reactions were monitored at 300 nm and the total analysis time per sample was 16 minutes.

The bottle containing both imipenem and cysteine showed a reduction of imipenem of approximately 70%, 85%, 89% and 91% after 20, 40, 60, and 90 minutes, respectively (see Table 1). However, after 90 minutes the bottle containing only imipenem showed no reduction in imipenem (see Figure Table 2).

TABLE 1

| Imipenem + Cysteine Reaction | | |
| --- | --- | --- |
| Reaction time (min) | Peak area at 10.88 min | % Change From T = 0 |
| 0 | 1619342 | — |
| 20 | 481363 | −70 |
| 40 | 251741 | −85 |
| 60 | 179565 | −89 |
| 90 | 146769 | −91 |

TABLE 2

| Imipenem + No Cysteine Control | | |
| --- | --- | --- |
| Reaction time (min) | Peak area at 10.88 min | % Change From T = 0 |
| 0 | 1619342 | — |
| 20 | 1756343 | +8.5 |
| 40 | 1795587 | +11 |
| 60 | 1798536 | +11 |
| 90 | 1737014 | +7 |

Example 2

Growth Performance in Resin Bottle Containing Imipenem with and without Cysteine An imipenem solution was prepared by dissolving 4.0 mg of imipenem into 100 mL of phosphate buffered saline (PBS), pH 7.0, and sterile filtered through a 0.2μ filter. Cysteine was prepared by dissolving 300 mg into 10 mL PBS and sterile filtered through a 0.2μ filter to achieve a final concentration in BacT/Alert® bottles (bioMerieux Inc, Missouri, USA) of 4 mM with the addition of 500 μL. A culture of *S. aureus* was prepared after overnight incubation to a final concentration of 30-300 CFU (colony forming units)/500 μL.

BacT/Alert® culture bottles (bioMerieux Inc, Missouri, USA) containing resin adsorbents were prepared for evaluation in triplicate as follows:

Growth controls were prepared by adding 10 mL of sterile filtered PBS alone or 10 mL of sterile filtered PBS plus 500 μL of cysteine solution. A control for the imipenem activity was prepared by adding 10 mL of imipenem solution. The imipenem/cysteine reaction was prepared by adding 10 mL of imipenem solution plus 500 μL of cysteine solution. Each bottle received 500 μL of the *S. aureus* culture and was then placed in a BacT/Alert 3D® instrument (bioMerieux Inc, Missouri, USA) at 36° C. and monitored for growth over five days.

After 5 days all the bottles containing imipenem without cysteine were negative for *S. aureus* growth. However, within 28 hours 2 of the 3 bottles containing both imipenem and cysteine were positive for *S. aureus* growth.

That which is claimed is:

1. A method for the neutralization and/or inactivation of an antimicrobial in a culture medium, the method comprising adding one or more non-thiol containing primary amines to said culture medium capable of supporting growth of microorganisms, wherein said one or more non-thiol containing primary amines are present in an amount effective for neutralization and/or inactivation of any antimicrobials that may be present in said culture medium, and wherein said one or more non-thiol containing primary amines are selected from the group consisting of methylamine, ethanolamine, trisamine, propylamine, 2-aminoheptane, 2 amino-2-methyl-1,3 propanediol, 2-amino-2-methyl-1-propanol, n-amylamine, benzylamine, 1,4-butanediamine, n-butylamine, cyclohexylamine, ethylamine, ethylenediamine, α-methylbenzylamine, phenethylamine, isopropylamine, butylamine, sec-butylamine, iso-butylamine, and tris(hydroxymethyl) aminomethane.

2. The method of claim 1, wherein said culture medium further comprises one or more adsorbents effective for neutralizing and/or inactivating any additional antibiotics present.

3. The method of claim 1, wherein a test sample suspected of containing microorganisms is added to said culture medium and cultured under conditions sufficient for growth of any microorganisms.

4. The method of claim 1, wherein said antibiotics comprise one or more β-lactam antibiotics and wherein said β-lactam antibiotics are selected from the group consisting of β-lactam antibiotics include, but are not limited to, penicillins, cephalosporins, monobactams, carbapenems and derivatives thereof.

5. The method of claim 1, wherein said non-thiol containing primary amine is hydroxylamine.

6. The method of claim 1, wherein said non-thiol containing primary amine is immobilized on a solid support and wherein said solid support is nitrocellulose, silica, polystyrene, polypropylene, polyvinyl chloride, EVA, glass, carbon, glassy carbon, carbon black, carbon nanotubes or fibrils, platinum, palladium, gold, silver, silver chloride, iridium, rhodium, or a polymeric carrier.

7. The method of claim 1, wherein said one or more non-thiol containing primary amines are present at a final concentration of from about 0.5 g/L to about 20 g/L.

* * * * *